United States Patent [19]

Pillot

[11] Patent Number: 4,871,659
[45] Date of Patent: Oct. 3, 1989

[54] REAGENT FOR DETECTING NON-A, NON-B VIRAL HEPATITIS (NANBH) AND AN IMMUNOENZYMATIC METHOD FOR DETECTING NANBH ANTIGENS IN FECAL EXTRACTS

[75] Inventor: Jacques Pillot, Gif-Sur-Yvette, France

[73] Assignee: Institut Pasteur, Paris, France

[21] Appl. No.: 35,172

[22] Filed: Apr. 7, 1987

[30] Foreign Application Priority Data

Apr. 16, 1986 [FR] France ................................ 86 05437

[51] Int. Cl.⁴ .................. G01N 33/569; G01N 33/535
[52] U.S. Cl. .......................................... 435/5; 435/7; 435/810; 436/513; 436/531; 436/820; 436/808; 422/61
[58] Field of Search ............... 435/5, 7, 810; 436/513, 436/531, 820, 808; 422/61

[56] References Cited

U.S. PATENT DOCUMENTS 4,464,474  8/1984  Coursaget ...................... 436/820 X
4,535,057  8/1985  Dreesman ...................... 436/531 X
4,702,909  10/1987  Villarejos ........................ 436/820 X
4,717,654  1/1988  Savoca ..................................... 435/7

FOREIGN PATENT DOCUMENTS 0068465  1/1983  European Pat. Off. .
0154392  9/1985  European Pat. Off. .
WO80/02598  11/1980  PCT Int'l Appl. .

OTHER PUBLICATIONS

Wong et al., Epidemic and Endemic Hepatitis in India: Evidence for a Non-A, Non-B Hepatitis Virus Aetiology, *Lancet* 1980; 2:876-879.
Kane et al., Epidemic Non-A, Non-B Hepatis in Nepal, *JAMA* 1984; vol. 252, pp. 3140-3145.

*Primary Examiner*—Christine M. Nucker
*Attorney, Agent, or Firm*—Finnegan, Henderson, Farabow, Garrett & Dunner

[57] ABSTRACT

Anti-NANBH (anti-non-A, non-B hepatitis) antibody comprises IgM isolated from sera of monkeys artificially infected with extracts of feces from patients known to be suffering from epidemic NANB hepatitis. A process for isolating an antibody of this type is provided. A reagent for detecting epidemic NANB hepatitis comprises the anti-NANBH IgM fixed to a solid support. The reagent is useful for diagnosing epidemic NANB viral hepatitis by forming an immunological complex between the anti-NANBH IgM and antigen in a fecal extract from a patient being diagnosed, and then incubating the immunological complex with enzyme-labeled IgG from serum of a human convalescing from epidemic NANBH. The complex is detected by developing the enzyme.

12 Claims, No Drawings

REAGENT FOR DETECTING NON-A, NON-B VIRAL HEPATITIS (NANBH) AND AN IMMUNOENZYMATIC METHOD FOR DETECTING NANBH ANTIGENS IN FECAL EXTRACTS

BACKGROUND OF THE INVENTION

The present invention relates to a novel reagent for detecting non-A, non-B viral hepatitis NANBH and to a process for diagnosing this type of hepatitis by an immunoenzymatic method.

Non-A, non-B hepatitis is defined as being viral infectious hepatitis, which cannot be attributed to hepatitis A virus (HAV), or to hepatitis B virus (HBV), or to other known human hepatotropic viruses, such as cytomegalovirus, Epstein-Barr virus or yellow fever virus. Non-A, non-B hepatitis seems to represent a group of diseases due to several different viruses.

In Western Europe and North America, 95% of transfusion hepatitis cases are due to infectious agents which are transmitted parenterally in the same way as hepatitis B, as reported by E. TABOR [Lancet, 1985, i: 743–745] and D.G. Wong et al. [Lancet, 1980, ii: 876–879].

Recent epidemiological data have demonstrated the existence of forms of NANBH which are transmitted like hepatitis A, i.e. by the fecal-oral route and virtually never by transfusion. Several epidemics of this type have been reported (M. S. Balayan et al.; Intervirology, 1983, 20: 23-31 - E. H. Belabbes et al.; J. Med. Virol., 1985, 16: 257–263 - M. A. Kane et al.; JAMA, 1984, 252: 3140–3145 - M. S. Khuroo; Am. J. Med., 1980, 68: 818–824). These epidemics are due to the water supply, with a fecal-oral mode of transmission. Viral particles of 27 nm have been observed by electron microscopy in samples obtained from patients' feces (M. S. Balayan et al.; Intervirology, 1983, 20:23–31 - M. A. Kane et al.; JAMA, 1984, 252: 3140–3145).

Non-A, non-B hepatitis viruses are known to cause serious liver diseases, such as cirrhosis of the liver, non-established malignant hepatoma and the like, so identification of these viruses and detection of the antigen-antibody system associated with these viruses is of the greatest importance in effecting an early diagnosis and rapidly adopting a suitable prophylaxis.

The diagnostic reagents and methods proposed hitherto essentially involve detection of the antigen associated with a non-A, non-B hepatitis virus transmitted during blood transfusions.

Thus, SHIRASHI et al. [THE LANCET, 21 Oct. 1978, p. 853–856] detected an antigen-antibody system, by counterelectrophoresis, in humans suffering from non-A, non-B hepatitis following a transfusion. PCT international application published under number 80/02598, filed on 20 May 1980 and claiming US priority of application Ser. No. 040,921 of 21 May 1979, applied the work of SHIRASHI et al., claiming an immunological test for detecting an antigen associated with non-A, non-B hepatitis (NANBH), in which a sample of serum from a supposedly affected mammal is reacted with an antibody originating from the serum of a donor mammal known to be carrying a NANBH infection, and the presence of the NANBH antigen is detected either indirectly via the immunoprecipitin formed by counterelectrophoresis, or by direct methods, such as radioimmunoassay, diffusion in gelose gel, passive hemagglutination, agglutination on latex, complement fixation or the ELISA test.

Furthermore, PCT international application no. WO 82/00205 describes a viral particle of 50 to 60 nm in diameter which possesses a nucleus of about 40 nm in diameter and is said to be the agent causing non-A, non-B hepatitis. Four samples containing this viral particle were deposited in the American Type Culture Collection under the numbers VR-2011, VR-2012, VR-2013 and VR-2014.

The particles described can be radiolabeled for use in a detection test.

Other authors have attempted to isolate the antigen associated with NANBH and to use this isolated antigen to prepare a reagent for diagnosing the infections caused by the virus of NANB viral hepatitis. In particular, French Patent 81 06385 of 20 Mar. 1981, in the name of TREPO, describes the isolation of a novel NANBH antigen by ultracentrifugation of sera or liver extracts, treatment of the centrifugation residue with a non-ionic detergent, and then fractionation in order to isolate the fractions containing purified NANBc antigen (this being followed, if appropriate, by treatment with an ionic detergent in order to isolate the AgNANBe). According to an alternative proposal corresponding to a variant in the said French patent, after any viral particles present have been removed by ultracentrifugation, as above, the gamma-globulins are removed, the AgNANBe is concentrated by precipitation, the concentrated fractions containing the AgNANBe are chromatographed on a support to which heparin is fixed, and the AgNANBe is collected in the eluates. The diagnostic reagents according to the TREPO French patent comprise a solid support to which at least one NANBc, NANBe or NANBs antigen and/or at least one anti-NANBc, anti-NANBe or anti-NANBs specific antibody are fixed; in the particular case of the diagnostic reagent whose support carries anti-(human gamma-globulin) antibodies, the antigen is separate from the support and can only be fixed via the corresponding antibodies in the serum to be tested, if they are present.

Similarly, the European Patent Application published under the number 66 296, in the name of EISAI, filed on 2 June 1982 and claiming a Japanese priority of 2 June 1981, describes the isolation of an antigen associated with NANB hepatitis by purification from liver taken by autopsy from patients who have died of NANB hepatitis, by conventional methods of protein fractionation, including ultracentrifugation, and defines this antigen by its physicochemical properties; the antigen according to the said European patent application is conjugated with a substance which may consist of particles of substrate suitable for passive hemagglutination, such as sheep erythrocytes, tracer isotopes for radioimmunoassays, or enzymes suitable for carrying out the ELISA test.

To date, however, no means seem to have been proposed which make it possible to identify an antigenantibody system associated with an epidemic form of NANB hepatitis.

SUMMARY OF THE INVENTION

The object of the present invention is to provide a reagent which is capable of making it possible to detect epidemic NANB viral hepatitis, and a diagnostic process using this reagent.

The present invention relates to an anti-NANBH antibody consisting of IgM's isolated from sera of monkeys artificially infected with extracts of feces from patients known to be suffering from epidemic NANB hepatitis.

The present invention also relates to a process for isolating an anti-NANBH antibody from sera of monkeys artificially infected by the ingestion of extracts of feces from patients suffering from epidemic NANB hepatitis, wherein the said sera are treated by chromatography on a column of dextran gel in 0.1 M Tris-NaCl buffer, pH 8.0, in order to isolate anti-NANBH IgM's.

In one embodiment of the process for isolating the anti-NANBH IgM's, according to the present invention, the sera of artificially infected monkeys used are sera taken as from the 27th day after inoculation.

The present invention also relates to a reagent capable of making it possible to detect epidemic NANB viral hepatitis, which comprises anti-NANBH IgM's fixed to solid supports and especially to polyvinyl chloride (PVC) plates.

The present invention also relates to a process for the preparation of a reagent capable of making it possible to detect epidemic NANB viral hepatitis, wherein the anti-NANBH IgM's isolated according to the invention are fixed to solid supports, and especially to PVC plates, by being brought into contact, at concentrations of the order of 50 μg of proteins per ml of PBS, with the said solid supports for 18 to 24 hours at 4° C.

In one embodiment of the process for the preparation of a reagent for detecting epidemic NANB viral hepatitis, according to the invention, the PVC plates covered with anti-NANBH IgM's are then coated with a layer of PBS containing 0.1% of BSA and 0.1% of "Tween 20".

The present invention also relates to a method for diagnosing epidemic NANB viral hepatitis, wherein the detection reagent consisting of the plates coated with IgM's is incubated with feces extracts for 1 hour at 37° C. and then with IgG fractions purified from sera of patients convalescing from epidemic NANBH, and labeled with an enzyme, in the presence of an appropriate developing substrate.

In a preferred embodiment of the diagnostic method according to the invention, the IgG fractions are labeled with β-galactosidase and the appropriate developing substrate preferably consists of orthonitro- phenyl-β-D-galactopyranoside.

The present invention also relates to IgG's labeled with an enzyme and intended for use, in association with the anti-NANBH IgM's according to the invention, for detecting epidemic NANB viral hepatitis, the said IgG's originating from sera of patients convalescing from epidemic NANB hepatitis.

The present invention further relates to a process for the preparation of these IgG's, which consists in purifying sera of patients convalescing from epidemic NANBH, by chromatography on a column of DEAE-Trisacryl, and then labeling the IgG's isolated in this way with an appropriate enzyme, preferably with β-galactosidase, by methods known per se.

Apart from the foregoing provisions, the invention also includes other provisions which will become apparent from the following description.

DETAILED DESCRIPTION OF PREFERRED EMBODIMENT

The invention will be understood more clearly with the aid of the following additional description, which refers to an example of how the process forming the subject of the present invention is carried out.

It must be clearly understood, however, that this example is given solely in order to illustrate the object of the invention and does not in any way imply a limitation.

EXAMPLE

1 - Determination of the NANB character of the hepatitis virus used as the startinq material Samples of sera were taken from 37 patients supposedly suffering from acute epidemic NANB viral hepatitis, in the region of TORTIYA in the IVORY COAST, during the first week of jaundice.

These samples were subjected to the following detection tests in order to establish the NANB character of the virus with certainty:

tests for detecting hepatitis A virus and hepatitis B virus with the aid of the commercially available ELISA kits produced by ABBOTT Laboratories (CHICAGO, Ill.), namely:

HAVAB test for detecting anti-A virus IgG's or IgM's,

"AUSZYME" test for detecting AgHBs,

HBe-EIA test for detecting AgHBe,

"CORZYME" test for determining the total antibodies directed against the capsid of hepatitis B virus, "CORZYME M" test for determining the specific IgM's directed against the capsid of hepatitis B virus, immunoenzymatic tests according to SCHMITZ et al. [J. Gen. Virol., 1980, 50: 59–68] for determining the antibodies directed against cylomegalovcius CMV, determination of the IgM's directed against Epstein-Barr virus by immunofluorescence according to GARDNER et al. in "Rapid virus diagnosis: application of immunofluorescence", published by BUTTERWORTHS, LONDON, 1980, p.276–278, and determination of the anti-yellow fever IgM's by immunocapture according to the technique of LHUILLIER et al., Ann. Virol. (Inst. Pasteur), 1983, 134E, p. 349–359.

The 37 samples of sera tested, originating from patients supposedly suffering from NANBH, all contained anti-HAV antibodies but none contained anti-HAV specific antibodies belonging to the class of the IgM's.

32 out of 37 sera possessed anti-HBc antibodies (antibodies directed against the antigen of the capsid of hepatitis B virus), but none had anti-HBc specific antibodies belonging to the class of the IgM immunoglobulins.

Two patients gave a positive test in the detection of the surface antigen of hepatitis B (AgHBs), but also a negative test in the detection of the AgHBe antigen peculiar to hepatitis B.

These serological results ruled out the possibility that hepatitis A or hepatitis B viruses were the cause of the epidemic of which the above-mentioned patients were victims, nor were specific antibodies found belonging to the class of the IgM's, anti-CMV, anti-Epstein-Barr virus or anti-yellow fever.

2 - Preparation of feces extracts 2.1. Samples of stool were taken from 10 patients (out of the 37 subjects) during the first few days after the symptoms of the disease appeared. They were used to prepare 10% feces extracts in PBS containing 1% of human serum albumin. These feces extracts were homogenized and then clarified by centrifugation.

2.2. The clarified feces extracts were filtered through a 0.45 μm millipore filter and then through filters consisting of 0.22 μm HA-type membrane discs, after which they were reacted with an equal volume of IgM fractions originating from sera of monkeys infected as described in 2.3. below, for 1 hour at 37° C. and then overnight at 4° C. The reaction mixture is centrifuged for 20 minutes at 20,000 g and the residue is suspended in PBS. An aliquot of this preparation is dialyzed against distilled water, negatively stained with phosphotungstic acid at pH 7.2 and then examined under a SIEMENS electron microscope.

2.3. The clarified feces extracts were diluted in water to a concentration of 10% in order to prepare an inoculum, which was administered orally at a dosage of 2 ml to 4 anesthetized African monkeys (3 Ceropithecus aethiops and 1 Erythrocebus patas).

Samples of sera and feces from these monkeys were collected before administration of the inoculum and on the 27th day after inoculation.

3 - Preparation of anti-NANBH IgM's 3.1. The anti-NANBH IgM's were isolated from sera of monkeys infected as described in 2.3. above, by chromatography on "SEPHADEX G-200" (agarose gel manufactured by PHARMACIA) in 0.1 M Tris-NaCl buffer, pH 8.0.

3.2. The isolated anti-NANBH IgM's were fixed to PVC plates (supplied by NUNC-IMMUNO-PLATES, DENMARK) by bringing these plates into contact, for 24 hours at 4° C., with the IgM's at a concentration of 50 μg of proteins/ml in PBS.

The plates treated in this way were then covered with PBS containing 0.1% of BSA and 0.1% of "Tween 20".

4 - Preparation of an IgG fraction for identifying the antigen-antibody system associated with the epidemic form of NANB hepatitis An IgG fraction was obtained by purifying sera of patients convalescing from NANBH, by chromatography on a column of DEAE-Trisacryl, and the purified IgG's obtained were then labeled with β-galactosidase.

5 - Test for diagnosing NANBH 5.1. IgM's isolated from monkey sera collected prior to inoculation were used to coat PVC plates for use as controls.

5.2. Extracts of feces from patients for whom an attempt is being made to establish the diagnosis of NANB hepatitis, prepared as described in 2.1. above (1:20 v/v), were incubated on plates coated with anti-NANBH IgM's, as described above (in 3.2.), for 1 hour at 37° C., and then with a fraction of IgG's (200 μg/ml) labeled with β-galactosidase, obtained as described in 4 above, in the presence of orthonitrophenyl-β-D-galactopyranoside as the developing chromogenic substrate.

5.3. The specific IgM's isolated from monkey sera taken on the 27th day after inoculation of the monkeys specifically fix the antigen present in the feces of patients suffering from NANB hepatitis, and the antigen fixed in this way is detected by the IgG's labeled with the enzyme, as described above.

6 - Results

In 5 out of 10 of the extracts of feces taken from patients supposedly suffering from NANBH, as described in 2.1. above, it was possible to detect the antigen associated with NANBH, but it could not be detected in any of the 30 extracts of feces originating from European patients suffering from other gastrointestinal infections (cf. table below). All the samples which were positive in the immunoenzymatic test using IgM's isolated 27 days after inoculation had been found to be negative in the control system which used IgM's isolated from sera taken before inoculation. The agglutination of what were probably viral particles was observed under the electron microscope after reaction of the IgM antibody isolated from sera of 4 patients with extracts of feces from the same patients.

As shown in the table below, there is no serological relationship between epidemic NANB hepatitis antigen present in the feces of infected patients and hepatitis A virus or hepatitis B antigen. This table in fact shows the results obtained in the immunoenzymatic test for detecting the presence of NANB antigen in samples of feces:

3 out of the 4 IgM antibodies isolated from sera of experimentally infected monkeys, fixed to a solid phase (PVC plate), specifically fix an antigen present in the samples of feces from patients presenting with an epidemic form of NANB hepatitis.

Two IgG fractions isolated from sera of patients convalescing from an epidemic form of NANB hepatitis were labeled with β-galactosidase and used as developers (* the results obtained with the 2nd fraction are parallel with those obtained with the 1st fraction). The results collated in the table are expressed as the P/N ratio (which is the ratio of the absorption of the sample tested to the absorption of the mean of the negative controls). 6 different extracts of normal feces were used as negative controls. Negative results (P/N<2.1) were obtained for control tests performed on plates covered with IgM's isolated from monkey sera prior to inoculation of the monkeys.

TABLE

IMMUNOENZYMATIC DETERMINATION OF THE ANTIGEN ASSOCIATED WITH EPIDEMIC NANB HEPATITIS

| Sample of feces | Monkey no. 1 | Monkey no. 2 | Monkey no. 3 |
|---|---|---|---|
| 1 | 2.18 | 4.98 | 2.1 |
|   |      | 6.20 |     |
| 2 | 2.1 | 6.37 | 3.13 |
|   |     | 4.25* | 3.19 |
| 3 | 18.5* | 4.37 | 3.36 |
|   |       | 4.66 |      |
| 4 | 6.06 | 2.35 | 2.1 |
|   | 17.7* | 3.25* |    |
| 5 | 2.1 | 2.1 | not determined (n.d.) |
| 6 | 6.39 | 5.20 | 6.22 |
| 7 | 2.1 | n.d. | 2.1 |
| 8 | 2.17 | 2.1 | n.d. |
| 9 | 2.1 | 2.1 | n.d. |
| 10 | 2.1 | 2.1 | n.d. |

*See section 6, "Results", page 10

The identification of epidemic NANB hepatitis virus on which the present invention is based has demonstrated that the supposed etiological agent of this form of hepatitis is unrelated both to hepatitis A virus and to hepatitis B virus, and that it is different from the two types of NANB hepatitis transmitted by blood transfusions.

According to the invention, IgM's isolated from sera of infected mammals make it possible to perform tests for diagnosing NANB hepatitis by immunoenzymatic characterization of an antigen associated with NANBH virus present in the feces of patients suffering from an epidemic form of NANB hepatitis.

As is evident from the foregoing description, the invention is in no way limited to those methods of implementation, embodiments and methods of application which have now been described more explicitly; on the contrary, it encompasses all the variants thereof which may occur to those skilled in the art, without departing from the framework or the scope of the present invention.

What is claimed is:

1. A method for diagnosing epidemic non-A, non-B hepatitis (NANBH) virus infection, wherein the method comprises:
    (A) providing IgM isolated from serum of a monkey artificially infected with an extract of feces from a patient known to be suffering from epidemic NANBH, wherein the IgM is fixed to a solid support;
    (B) providing enzyme-labeled, purified IgG form serum of a patient convalescing fom epidemic NANBH;
    (C) incubating the IgM for 1 hour at 37° C. with a fecal extract from a human to be diagnosed, to thereby form an immunological complex;
    (D) incubating the enzyme-labeled IgG with the immunological complex in order to bind the IgG to the complex; and
    (E) developing the enzyme with a substrate for the enzyme.

2. Method as claimed in claim 1, wherein the solid support is comprised of polyvinyl chloride.

3. Method as claimed in claim 1, wherein the IgM is from serum of the monkey taken as from the 27th day after the artificial infection.

4. Method as claimed in claim 1, wherein the enzyme is β-galactosidase and the substrate for the enzyme is orthonitrophenyl-β-D-galactopyranoside.

5. A method for diagnosing epidemic non-A, non-B hepatitis (NANBH) virus infection, wherein the method comprises:
    (A) providing IgM isolated from serum of a monkey artificially infected with an extract of feces from a patient known to be suffering from epidemic NANBH, wherein the IgM is fixed to a polyvinyl chloride plate;
    (B) providing purified IgG from serum of a patient convalescing from epidemic NANBH, wherein the IgG is labeled with β-galactosidase enzyme;
    (C) incubating the IgM for 1 hour at 37° C. with a fecal extract from a human to be diagnosed, to thereby form an immunological complex;
    (D) incubating the enzyme-labeled IgG with the immunological complex in order to bind the IgG to the complex; and
    (E) developing the enzyme with orthonitrophenyl-β-D-galactopyranoside.

6. Method as claimed in claim 5, wherein the IgM is from serum of the monkey taken as from the 27th day after the artificial infection.

7. A kit for diagnosing epidemic non-A, non-B hepatitis (NANBH) virus infection, wherein the kit comprises:
    (A) IgM isolated from serum of a monkey artificially infected with an extract of feces from a patient known to be suffering from epidemic NANBH, wherein the IgM is fixed to a solid support;
    (B) a container containing enzyme-labeled, purified IgG from serum of a patient convalescing from epidemic NANBH; and
    (C) a container containing a substrate for the enzyme.

8. Kit as claimed in claim 7, wherein the solid support is comprised of polyvinyl chloride.

9. Kit as claimed in claim 7, wherein the IgM is from serum of the monkey taken as from the 27th day after the artificial infection.

10. Kit as claimed in claim 7, wherein the enzyme is β-galactosidase and the substrate for the enzyme is orthonitrophenyl-β-D-galactopyranoside.

11. Kit as claimed in claim 7, wherein the IgM is fixed to a polyvinyl chloride plate, and the IgG is labeled with β-galactosidase enzyme, and the substrate for the enzyme is orthonitrophenyl-β-D-galactopyranoside.

12. Kit as claimed in claim 11, wherein the IgM is from serum of the monkey taken as from the 27th day after the artificial infection.

* * * * *